(12) United States Patent
Hayashi et al.

(10) Patent No.: US 10,119,908 B2
(45) Date of Patent: Nov. 6, 2018

(54) PARTICLE SENSOR

(71) Applicant: PANASONIC INTELLECTUAL PROPERTY MANAGEMENT CO., LTD., Osaka (JP)

(72) Inventors: Shintaro Hayashi, Hyogo (JP); Shinichi Kitaoka, Osaka (JP); Hirotaka Matsunami, Osaka (JP)

(73) Assignee: PANASONIC INTELLECTUAL PROPERTY MANAGEMENT CO., LTD., Osaka (JP)

( * ) Notice: Subject to any disclaimer, the term of this patent is extended or adjusted under 35 U.S.C. 154(b) by 0 days.

(21) Appl. No.: 15/383,155

(22) Filed: Dec. 19, 2016

(65) Prior Publication Data

US 2017/0176329 A1 Jun. 22, 2017

(30) Foreign Application Priority Data

Dec. 21, 2015 (JP) .................................. 2015-248799

(51) Int. Cl.
| | |
|---|---|
| *G01N 21/53* | (2006.01) |
| *G01J 1/04* | (2006.01) |
| *G01J 1/02* | (2006.01) |
| *G01N 21/47* | (2006.01) |
| *G01N 15/00* | (2006.01) |
| *G01N 15/06* | (2006.01) |
| *G01N 15/14* | (2006.01) |

(52) U.S. Cl.
CPC ............ *G01N 21/53* (2013.01); *G01J 1/0214* (2013.01); *G01J 1/0418* (2013.01); *G01N 15/1459* (2013.01); *G01N 2015/0046* (2013.01); *G01N 2015/0693* (2013.01); *G01N 2015/1486* (2013.01); *G01N 2021/473* (2013.01)

(58) Field of Classification Search
CPC ................. G01J 1/0418; G01J 1/0214; G01N 2021/473; G01N 21/53
USPC .................................................. 356/335–343
See application file for complete search history.

(56) References Cited

U.S. PATENT DOCUMENTS

| | | | |
|---|---|---|---|
| 5,043,591 | A | 4/1991 | Ludlow et al. |
| 5,089,714 | A | 2/1992 | Ludlow et al. |
| 5,467,189 | A | 11/1995 | Kreikebaum et al. |
| 5,745,293 | A | 4/1998 | Lassalle |

(Continued)

FOREIGN PATENT DOCUMENTS

| | | |
|---|---|---|
| JP | 63-110992 | 7/1988 |
| JP | 7-37935 | 4/1995 |

(Continued)

*Primary Examiner* — Tri T Ton (74) *Attorney, Agent, or Firm* — Greenblum & Bernstein, P.L.C.

(57) ABSTRACT

A particle sensor is provided. The particle sensor includes a light projector that projects light to a detection area. A light receiver receives scattered light. The scattered light is light from the light projector that has been scattered by particles in the detection area. A first reflector reflects the scattered light to the light receiver. A light attenuator attenuates stray light that exits the first reflector. The first reflector includes a first aperture that introduces the light from the light projector into an interior of the first reflector and a second aperture that exits the stray light from the first reflector. The light attenuator includes a third aperture through which the stray light that exits the first reflector passes. An aperture area of the third aperture is smaller than an aperture area of the second aperture.

21 Claims, 4 Drawing Sheets

(56) References Cited

U.S. PATENT DOCUMENTS

| | | | |
|---|---|---|---|
| 5,929,988 | A | 7/1999 | Ichikawa |
| 6,184,537 | B1 | 2/2001 | Knox et al. |
| 2008/0218365 | A1 | 9/2008 | Kato |

FOREIGN PATENT DOCUMENTS

| | | |
|---|---|---|
| JP | 8-233736 | 9/1996 |
| JP | 9-189879 | 7/1997 |
| JP | 2771206 | 4/1998 |
| JP | 11-248628 | 9/1999 |
| JP | 11-248629 | 9/1999 |
| JP | 2000-235000 | 8/2000 |
| JP | 3358121 | 10/2002 |
| JP | 3436539 | 6/2003 |
| JP | 2008-224222 | 9/2008 |
| JP | 4802310 | 8/2011 |
| WO | 89/04472 | 5/1989 |
| WO | 95/09354 | 4/1995 |

PARTICLE SENSOR

CROSS REFERENCE TO RELATED APPLICATION

This application claims the benefit of priority of Japanese Patent Application Number 2015-248799 filed on Dec. 21, 2015 the entire content of which is hereby incorporated by reference.

BACKGROUND

1. Technical Field

The present disclosure relates to a particle sensor.

2. Description of the Related Art

Known particle sensors include a scattered light particle sensor that uses scattered light to detect airborne particles (aerosol).

A scattered light particle sensor is a photoelectric sensor including a light projector and a light receiver, and emits light via the light projector into gas introduced into the sensor as a target to be measured and detects particles in the gas by detecting light scattered by the particles. With this, airborne dust, pollen, smoke, and PM 2.5 (fine particulate matter), for example, can be detected.

There is a problem with scattered light particle sensors that a portion of the light from the light projector becomes stray light (unwanted light) and reaches the light receiver, decreasing detection accuracy. A technique has been proposed that disposes a light trap (stray light trap) so as to oppose the light projector or the light receiver to reduce stray light (for example, see Japanese Unexamined Patent Application Publication No. H11-248629 and Japanese Unexamined Patent Application Publication No. 2000-235000).

SUMMARY

In recent years, use of a reflector (mirror) in particle sensors to improve detection efficiency has been considered. The reflector improves detection efficiency by reflecting and focusing the light scattered by particles onto the light receiver.

However, due to the significantly high focusing ability of the reflector, even if a slight amount of light leaks from the light trap, the leaked light is received by the light receiver as stray light, generating noise.

The present disclosure has been made in view of the above problem, and has an object to provide a particle sensor capable of reducing noise generated by stray light.

In order to achieve the above object, in one aspect, the particle sensor according to the present disclosure includes: a light projector that projects light to a detection area; a light receiver that receives scattered light, the scattered light being light from the light projector that has been scattered by particles in the detection area; a first reflector that reflects and guides the scattered light to the light receiver; and a light attenuator for attenuating light that exits the first reflector. The first reflector has a first aperture for introducing the light from the light projector into an interior of the first reflector and a second aperture through which light exits the first reflector. The light attenuator has a third aperture through which the light that has exited the first reflector through the second aperture passes. The aperture area of the third aperture is smaller than the aperture area of the second aperture.

According to the present disclosure, it is possible to reduce noise generated by stray light.

BRIEF DESCRIPTION OF DRAWINGS

The figures depict one or more implementations in accordance with the present teaching, by way of examples only, not by way of limitations. In the figures, like reference numerals refer to the same or similar elements.

DETAILED DESCRIPTION OF THE EMBODIMENT

Hereinafter, an embodiment according to the present disclosure will be described with reference to the drawings. Note that the embodiment described below shows a specific example of the present disclosure. The numerical values, shapes, materials, elements, the arrangement and connection of the elements, etc., indicated in the following embodiment are mere examples, and therefore are not intended to limit the inventive concept. Therefore, among the elements in the following embodiment, those not recited in any of the independent claims defining the most generic part of the inventive concept are described as optional elements.

Note that the respective figures are schematic diagrams and are not necessarily precise illustrations. Additionally, like reference signs indicate like elements. As such, overlapping explanations of like elements are omitted or simplified.

Moreover, in the description and figures, the X, Y, and Z axes refer to the three axes of the three dimensional coordinate system, where vertical directions correspond to the Z axis, and directions perpendicular to the Z axis (directions parallel to the XY plane) correspond to horizontal directions.

Embodiment

Figure 1:
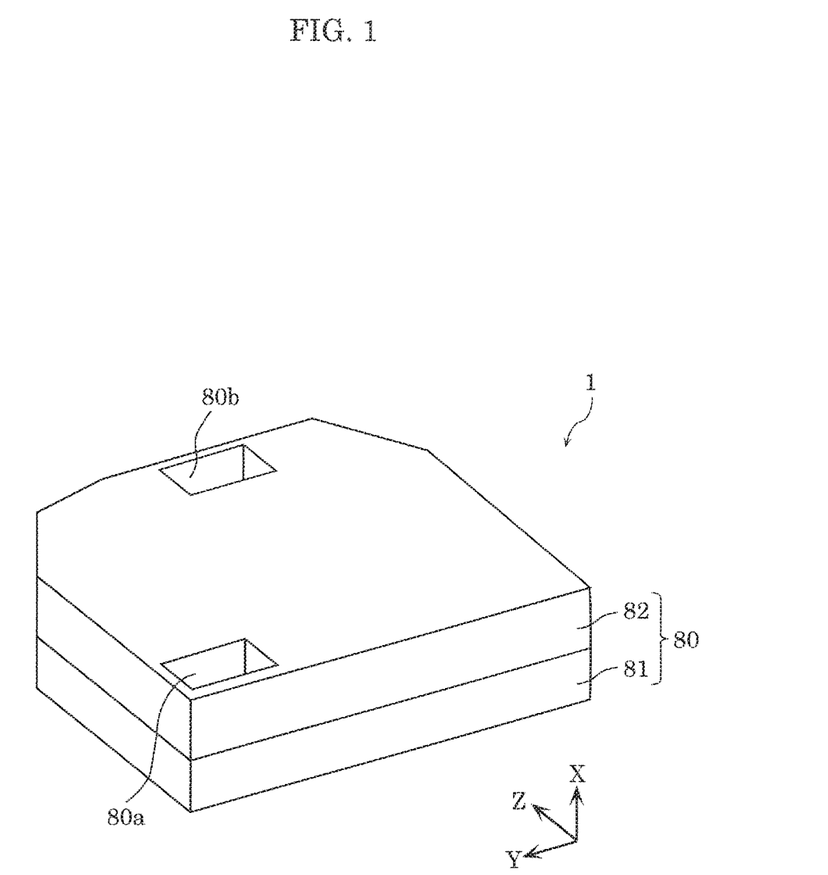
FIG. 1 is an external perspective view of a particle sensor according to an embodiment.
Figure 2:
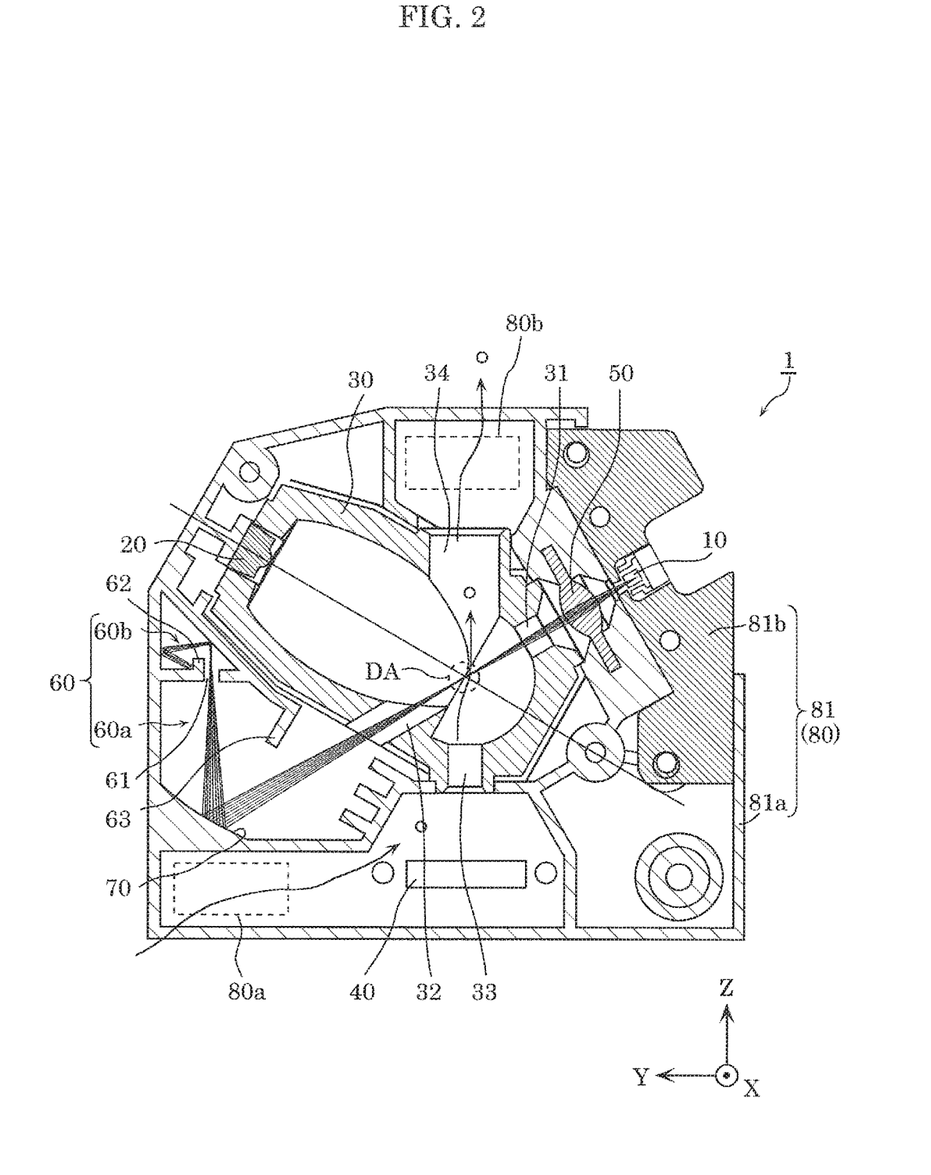
FIG. 2 is a cross sectional view of the particle sensor according to the embodiment.
Figure 3:
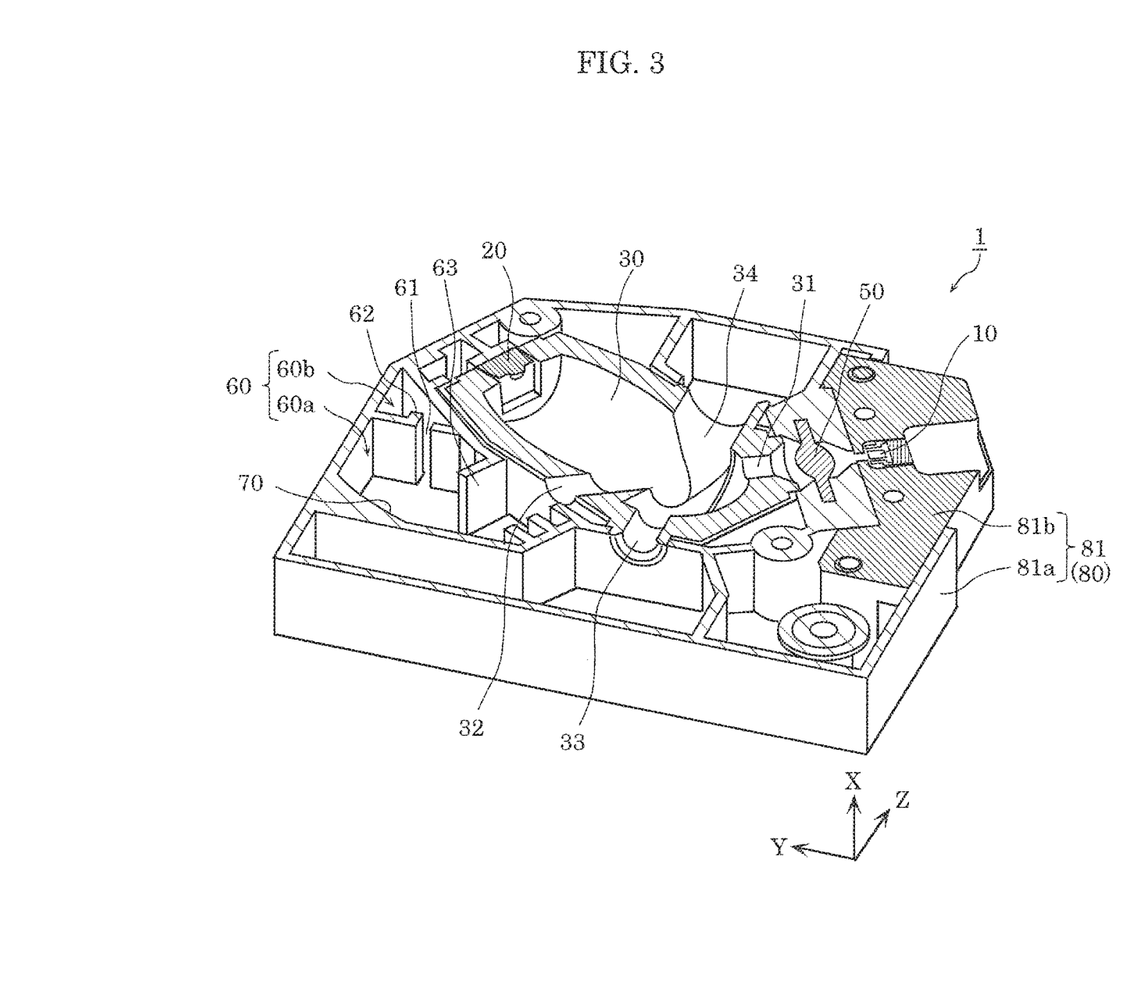
FIG. 3 is a cross sectional perspective view of the particle sensor according to the embodiment.

Particle sensor 1 according to this embodiment will be described with reference to FIG. 1 through FIG. 3. FIG. 1 is an external perspective view of particle sensor 1 according to this embodiment. FIG. 2 is a cross sectional view (in the YZ plane) of particle sensor 1. FIG. 3 is a cross sectional perspective view (in the XY plane) of particle sensor 1. Note that FIG. 2 shows traces of light beams emitted by light projector 10.

As illustrated in FIG. 2 and FIG. 3, particle sensor 1 is a photoelectric sensor that includes light projector 10 and light receiver 20, and detects airborne particles as a result of light receiver 20 receiving light that has been emitted by light projector 10 and scattered by particles in detection area DA. Particles targeted for detection by particle sensor 1 include, for example, dust, pollen, smoke, and PM2.5 that are 2 micrometers or finer. Particle sensor 1 can detect, for example, the presence or absence of particles, the number of particles, particle size, and particle concentration.

As illustrated in FIG. 2 and FIG. 3, particle sensor 1 includes light projector 10, light receiver 20, first reflector 30, heater 40, projection lens 50, light attenuator 60, and second reflector 70.

As illustrated in FIG. 1, particle sensor 1 includes housing 80, and as illustrated in FIG. 1 through FIG. 3, housing 80 houses light projector 10, light receiver 20, first reflector 30, heater 40, projection lens 50, light attenuator 60, and second reflector 70. Note that, as illustrated in FIG. 2, light projector 10 and light receiver 20 are disposed in housing 80 such that their respective optical axes intersect in detection area DA.

Detection area DA is an aerosol detection area for detecting particles (aerosol) dispersed in the gas to be measured. Detection area DA is also a scattered light region in which scattered light, which is light scattered by particles dispersed in gas, is formed. In other words, in detection area DA, light emitted by light projector 10 is reflected off particles dispersed in gas, resulting in scattered light. In this embodiment, detection area DA includes an area in which the optical axis of light projector 10 and the optical axis of light receiver 20 intersect, and is in a path along which particles in the interior of first reflector 30 travel. Detection area DA is, for example, 2 millimeters in diameter. As illustrated in FIG. 1 and FIG. 2, the gas to be measured enters via inlet 80a of housing 80, travels through detection area DA, and then exits through outlet 80b.

Light projector 10 projects light to detection area DA. Light projector 10 is a light source that emits light of a predetermined wavelength, and is a light emitter that emits, for example, infrared light, blue light, green light, red light, or ultraviolet light. A semiconductor light emitter such as an LED or LD (semiconductor laser) may be used as light projector 10. A red light LD that emits red light may be used as a low cost, high output light projector 10. Moreover, light projector 10 may be configured to emit mixed waves of two or more wavelengths. In this embodiment, the optical axis of light projector 10, for example, passes through detection area DA.

Note that the shorter the wavelength of light emitted by light projector 10 is, the easier it is to detect small diameter particles. Moreover, the method of controlling the emission of light by light projector 10 is not limited to a particular method; light emitted by light projector 10 may be continuous or pulsed light achieved by driving light projector 10 with direct current. Moreover, the output magnitude of light projector 10 may be temporally adjusted.

Light receiver 20 is a photodetector that receives light from light projector 10 that has been dispersed by particles dispersed in gas in detection area DA. In other words, light receiver 20 receives light that has been emitted by light projector 10 and reflected and scattered by particles in detection area DA. Light receiver 20 is an element that converts received light into an electric signal, such as a photodiode, photo IC diode, phototransistor, or a photomultiplier tube.

First reflector 30 reflects and guides, to light receiver 20, light from light projector 10 that has been scattered by particles in detection area DA. In this embodiment, first reflector 30 is a condensing mirror that reflects, guides, and focuses onto light receiver 20 light scattered by particles in detection area DA.

More specifically, first reflector 30 is an elliptical mirror whose inner surface (reflective surface) forms a segment of a spheroid (ellipsoid of revolution). The inner surface of first reflector 30 has a cross sectional shape of a segment of an ellipse. In this case, among the two focal points that define the ellipse of the spheroid formed by the inner surface of first reflector 30, one (the first focal point) is, for example, located in detection area DA, and the other (the second focal point) is, for example, located in the vicinity of light receiver 20 (for example, in the center of light receiver 20).

With this, light scattered by particles in detection area DA can strike light receiver 20 after reflecting only a low number of times (one time or several times). In other words, the attenuation of light due to the light reflecting many times can be avoided. This increases the light reception efficiency of light receiver 20 and thus increases particle detection efficiency. Note that the ellipse included of the spheroid defined by the shape of the inner surface of first reflector 30 has, for example, a major axis of 20 millimeters to 100 millimeters, and a minor axis of 10 millimeters to 50 millimeters.

The inner surface of first reflector 30 is a reflective surface, and, for example, may be a surface that is unlikely to scatter light and is low in absorptivity and high in reflectivity (e.g., a specular surface). With this, the majority of light incident on first reflector 30 can be guided to light receiver 20. First reflector 30 may include, for example, metal as a base material such that the inner surface thereof is itself a reflective surface, and, alternatively, may include resin or metal as a base material and a reflective film formed on the inner surface as the reflective surface. The reflective film may be a reflective metal film of, for example, aluminum, gold, silver, or copper, a specular film, or a dielectric multilayer film. More specifically, silver plating or aluminum vapor-deposited film may be used as the reflective film. Forming such a reflective film increases the reflectivity of the inner surface of first reflector 30.

First reflector 30 includes light entrance aperture (first aperture) 31 for introducing light from light projector 10 into the interior of first reflector 30, and light exit aperture (second aperture) 32 through which light exits first reflector 30. Light entrance aperture 31 is a through-hole for light from outside first reflector 30 to enter into the interior of first reflector 30, and light exit aperture 32 is a through-hole for light from the interior of first reflector 30 to exit out of first reflector 30. Light entrance aperture 31 and light exit aperture 32 are exemplified as, but not limited to, cylindrical through holes having circular openings.

Light entrance aperture 31 and light exit aperture 32 are provided on the optical axis of light projector 10. In other words, light entrance aperture 31 and light exit aperture 32 are provided across from each other with detection area DA therebetween. Therefore, light that has been emitted by light projector 10, entered first reflector 30 through light entrance aperture 31, and not been scattered by particles in detection area DA continues travelling in a straight line through first reflector 30 and exits first reflector 30 through light exit aperture 32.

Moreover, first reflector 30 includes particle entrance aperture 33 for introducing into the interior of first reflector 30 particles which have entered housing 80 through inlet 80a, and particle exit aperture 34 through which particles in the interior of first reflector 30 exit first reflector 30. In other words, particle entrance aperture 33 and particle exit aperture 34 form a passage for particles (gas) inside housing 80 to pass along.

Particle entrance aperture 33 and particle exit aperture 34 are provided across from each other with detection area DA therebetween. More specifically, particle entrance aperture 33 and particle exit aperture 34 are provided along a vertically extending line (the Z axis). Particle entrance aperture 33 and particle exit aperture 34 are exemplified as, but not limited to, cylindrical through holes having circular openings.

Note that the interior of first reflector 30 may be filled with a light transmissive material. Examples of the light transmissive material include light transmissive resin, such as acrylic (PMMA) or polycarbonate (PC). However, in this case, there is a need to hollow out the portion corresponding to the path along which particles travel. Such a path can be formed, for example, as a hollow center of a cylinder extending from particle entrance aperture 33 toward particle exit aperture 34 and passing through detection area DA.

Heater 40 is a heater that heats gas (air), such as a heater resistor. As a result of heater 40 heating gas, an upward current (a flow of gas in the positive direction along the Z axis) inside housing 80 can be generated. With this, gas dispersed with particles can be easily introduced into housing 80 via inlet 80a and guided to detection area DA.

Projection lens 50 is disposed in front of light projector 10 and transmits light (the projected beam of light) from light projector 10 toward detection area DA. Light from light projector 10 reaches detection area DA after passing through projection lens 50. Projection lens 50 is, for example, disposed 3 millimeters to 5 millimeters from light projector 10, and the focal point of projection lens 50 is located approximately 16 millimeters from light projector 10.

Projection lens 50 is, for example, a condenser that condenses (focuses) light from light projector 10 in detection area DA. In other words, the focal point of projection lens (condenser) 50 is located in detection area DA, and in this embodiment, is the same as the focal point of the ellipse defining first reflector 30. Projection lens 50 is, for example, a resin lens made of a light transmissive resin such as acrylic (PMMA) or polycarbonate (PC), or a glass lens made of glass, and has a thickness of approximately 3 millimeters and a diameter of approximately 10 millimeters.

Light attenuator 60 has a light attenuating structure (light trap structure) for attenuating light. Light attenuator 60 is a component that attenuates unwanted light (stray light) inside light attenuator 60 by reflecting the unwanted light many times. In this embodiment, light attenuator 60 attenuates light that exits first reflector 30 via light exit aperture 32. With this, light that has entered light attenuator 60 from first reflector 30 can be attenuated in light attenuator 60 to keep the light from reentering first reflector 30.

In this embodiment, light attenuator 60 and light projector 10 are provided across from each other with detection area DA therebetween. More specifically, light attenuator 60 is an optical chamber disposed adjacent first reflector 30, and is spatially connected to first reflector 30 via light exit aperture 32 provided in first reflector 30.

Light attenuator 60 includes first space 60a and second space 60b. First space 60a and second space 60b are each enclosed spaces surrounded by walls, and each include an optical chamber having a light attenuating structure (light trap structure).

First space 60a and first reflector 30 are spatially connected via light exit aperture 32, and light that has exited first reflector 30 enters first space 60a. A plurality of pleated protrusions for attenuating light are formed on the inner wall surface of first space 60a as the light attenuating structure. For example, the plurality of protrusions are configured of approximately 1 millimeter thick plate-shaped extensions arranged in a row. Provision of a plurality of such protrusions makes it possible to trap and attenuate uncontrollable stray light such as scattered and reflected light. Note that the surfaces of the plurality of protrusions do not need to be processed, but surface processing may be performed to increase the light absorption rate. Moreover, the plurality of protrusions are not limited to the above shape, and may be wedge shaped.

Light attenuator 60 has through-hole 61 (third aperture), and first space 60a and second space 60b are spatially connected via through-hole 61. Light from first space 60a enters second space 60b through through-hole 61.

Through-hole 61 is an aperture through which light that has exited first reflector 30 through light exit aperture 32 passes. More specifically, light that has exited first reflector 30 through light exit aperture 32 enters first space 60a and is guided to second space 60b through through-hole 61. The light guided into second space 60b is attenuated in second space 60b. In other words, second space 60b is a light trap, and through-hole 61 is a light trap aperture.

The light attenuating structure of second space 60b for attenuating light by reflecting the light many times is configured of three walls that surround second space 60b. For example, the three wall surfaces that surround second space 60b form a right, triangle that form three angles of 30 degrees, 60 degrees, and 90 degrees. Note that the shape formed by the wall surfaces surrounding second space 60b is not limited to the right triangle described above; the shape may be a different triangle or a polygonal shape other than a triangle. Note that, although not illustrated in the drawings, a plurality of pleated or wedge shaped protrusions may be formed on the inner wall surface of second space 60b as a light attenuating structure, similar to first space 60a. This makes it possible to further effectively attenuate light that enters second space 60b.

The aperture area of through-hole 61 is smaller than the aperture area of light exit aperture 32. In this embodiment, through-hole 61 has a plan view shape of a rectangular slit whose width is, for example, approximately 0.2 millimeters to 1 millimeter. Forming through-hole 61 as a narrow slit makes it possible to reduce the percentage of light in second space 60b that exits second space 60b. Note that the plan view shape of through-hole 61 is not limited to a rectangular shape; through-hole 61 may have, for example, a circular plan view shape.

Moreover, protrusion 62 is disposed at an edge of through-hole 61, on the second space 60b side of through-hole 61, as a return bend. This makes it possible to reduce the percentage of light that enters second space 60b and then exits second space 60b back to first space 60a through through-hole 61.

Barrier 63 is disposed in first space 60a. Barrier 63 is disposed on a line connecting light exit aperture 32 and through-hole 61. In other words, one of light exit aperture 32 and through-hole 61 cannot be seen from the perspective of the other and vice versa due to barrier 63. Thus, even if light were to leak from second space 60b through through-hole 61, disposing barrier 63 in this manner makes it possible to prevent such light from directly returning to first reflector 30.

Second reflector 70 is disposed on light attenuator 60. More specifically, second reflector 70 is disposed in first space 60a of light attenuator 60.

Second reflector 70 is a reflective component that reflects and guides, to through-hole 61, light that has exited light exit aperture 32. In this embodiment, second reflector 70 is a condensing mirror that reflects, guides, and focuses onto through-hole 61 light that has exited first reflector 30 through light exit aperture 32. This makes it possible to introduce light that has exited through light exit aperture 32 into second space 60b. In other words, stray light (unwanted light) among light emitted by light projector 10 can be refocused in second space 60b through through-hole 61. Since through-hole 61 is a rectangular slit in this embodiment, a cylindrical mirror that focuses light that has exited through light exit aperture 32 into a beam that collects at through-hole 61 is provided as second reflector 70. In this case, the focal distance of second reflector 70 is, for example, 10 millimeters to 30 millimeters.

First reflector 30 and second reflector 70 are distanced from each other. More specifically, second reflector 70 is disposed in a location distanced from first reflector 30 by approximately 10 millimeters to 30 millimeters. Note that second reflector 70 is exemplified as, but not limited to, being inclined approximately 30 degrees to 50 degrees relative to the XY plane.

The inner surface of second reflector 70 is a reflective surface, and, for example, may be a surface that is unlikely to scatter light and is low in absorptivity and high in reflectivity (e.g., a specular surface). Second reflector 70 may include, for example, metal as a base material such that the inner surface thereof is itself a reflective surface, and, alternatively, may include resin or metal as a base material and a reflective film formed on the inner surface as the reflective surface. For example, second reflector 70 may be formed by forming a reflective film on the inner surface of housing 80. The reflective film may be a reflective metal film of, for example, aluminum, gold, silver, or copper, a specular film, or a dielectric multilayer film. More specifically, a silver plating or aluminum vapor-deposited film may be used as the reflective film. Forming such a reflective film increases the reflectivity of the inner surface of second reflector 70. Note that aluminum tape may be applied to the inner surface of housing 80 as a reflective film to form second reflector 70.

Housing 80 is a case that houses, for example, light projector 10, light receiver 20, first reflector 30, heater 40, and projection lens 50. More specifically, housing 80 is configured to retain, for example, light projector 10, light receiver 20, first reflector 30, heater 40, and projection lens 50. Housing 80 is a low profile, cuboid box-like case.

Housing 80 includes inlet 80a and outlet 80b. Gas dispersed with particles enters the interior of housing 80 through inlet 80a, passes through detection area DA, and exits housing 80 through outlet 80b. Inlet 80a is an air entrance aperture for introducing air into the interior of housing 80. Outlet 80b is an air exit aperture for expelling gas out of housing 80. Note that by designing the opening of inlet 80a to be larger in area than the opening of outlet 80b, air can efficiently be introduced into and expelled from housing 80.

Housing 80 includes first housing 81 and second housing 82. Moreover, first housing 81 includes first support 81a and second support 81b. First support 81a supports light receiver 20, first reflector 30, heater 40, and projection lens 50. Second support 81b supports light projector 10. First support 81a and second housing 82 are made of a resin material, and second support 81b is made of a metal material. First support 81a and second housing 82 are exemplified as, but not limited to, being made of a black colored ABS resin, and second support 81b is exemplified as, but not limited to, being made of aluminum. Note that light attenuator 60 is defined by the internal structure of first support 81a. For example, light attenuator 60 is formed in a predetermined shape by resin forming first support 81a.

In particle sensor 1 configured as described above, particles dispersed in a gas (air) introduced into the interior of particle sensor 1 (housing 80) can be detected by, for example, the following.

Gas introduced into the interior of housing 80 through inlet 80a is guided to detection area DA. Here, when particles are (aerosol is) dispersed in the gas, the light from light projector 10 reflects off the particles present in detection area DA. This produces scattered light. A portion of the light scattered by the particles is reflected off first reflector 30 and guided to light receiver 20. Light incident on light receiver 20 is converted into an electric signal and output. The electric signal indicates whether or not particles are present in the gas introduced into particle sensor 1.

Moreover, it is possible to determine the size (diameter) of the particles from the size of the signal received at light receiver 20—that is to say, from the intensity of the light scattered by the particles. Thus, it is possible to determine whether the particles dispersed in the air are dust, pollen, smoke, or PM2.5 (fine particulate matter) particles.

Furthermore, since each output of the signal detected by light receiver 20—in other words, each peak intensity of light scattered by the particles—corresponds to one particle, the number of particles in the gas introduced into particle sensor 1 and the particle concentration can be calculated.

However, when the air introduced into particle sensor 1 does not include any particles, there are no particles present in detection area DA, so the light from light projector 10 passes directly through detection area DA without being scattered by particles. Thus, in this case, there is typically no response by light receiver 20, and therefore it is determined that there are no particles present in the gas introduced into particle sensor 1.

Figure 4:
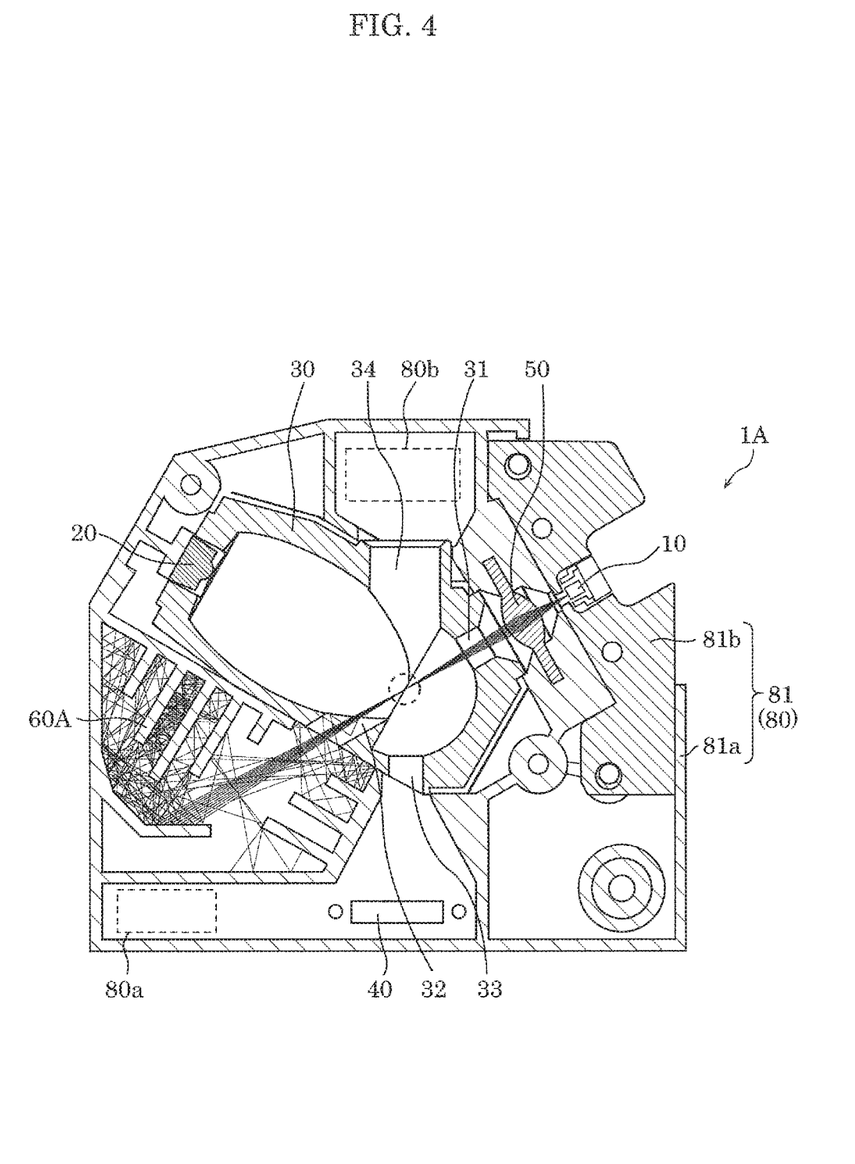
FIG. 4 is a cross sectional view of a particle sensor according to a comparative example.

Next, the advantageous effects of particle sensor 1 according to this embodiment will be described via comparison with a comparative particle sensor example. FIG. 4 is a cross sectional view of particle sensor 1A according to a comparative example. Note that FIG. 4 shows traces of light beams emitted by light projector 10.

Stray light (unwanted light) in the particle sensor (i.e., in the housing) is a source of noise. Therefore, stray light needs to be adequately attenuated to prevent it from reaching light receiver. For example, light emitted by light projector that passes through the detection area without being scattered by particles in the detection area becomes stray light. Therefore, the light that passes through the detection area needs to be adequately attenuated to prevent it from reaching the light receiver.

For example, the comparative example particle sensor 1A illustrated in FIG. 4 includes light attenuator 60A which has a light trap structure and is for attenuating light that passes through detection area DA. Light attenuator 60A is disposed across from light projector 10 with detection area DA therebetween. As the light trap structure, light attenuator 60A includes a plurality of protrusions configured of plate-shaped extensions arranged in a row.

However, with the comparative example particle sensor 1A illustrated in FIG. 4, the noise level, which is the ratio of the light input of light receiver 20 with respect to the light output of light projector 10 (light receiver 20 light input/light projector 10 light output), is approximately $10^{-5}$. An adequate noise level for a particle sensor is approximately $10^{-7}$. As such, the amount of attenuation of stray light is short by 2 digits.

In contrast, as illustrated in FIG. 2, with particle sensor 1 according to this embodiment, first reflector 30 includes light entrance aperture (first aperture) 31 for introducing light from light projector 10 into the interior of first reflector 30, and light exit aperture (second aperture) 32 through which light exits first reflector 30. Moreover, light attenuator 60 includes through-hole 61 (third aperture) through which light that has exited first reflector 30 through light exit aperture 32 passes, and the aperture area of through-hole 61 is smaller than the aperture area of light exit aperture 32.

This makes it possible to inhibit stray light that has exited first reflector 30 through light exit aperture 32 and passed through through-hole 61 from leaking back out through through-hole 61. Consequently, it is possible to inhibit stray light from returning to first reflector 30 and thus reduce noise generated by stray light. As a result, it is possible to realize a particle sensor that is highly accurate and efficient in regard to detection. For example, with the structure of particle sensor 1 illustrated in FIG. 2, the noise level was approximately $10^{-7}$.

Moreover, particle sensor 1 according to this embodiment includes barrier 63 disposed on a line connecting light exit aperture 32 and through-hole 61.

Thus, even if light were to leak through through-hole 61, it possible to prevent such light from directly returning to first reflector 30. In other words, even if light were to leak through through-hole 61 and return to first reflector 30, the leaked light from through-hole 61 would reflect in the internal structure before returning to first reflector 30, thereby attenuating the leaked light. This makes it possible to reduce noise generated by stray light even further.

Moreover, particle sensor 1 according to this embodiment includes second reflector 70 that reflects and guides, to through-hole 61, light that has exited first reflector 30 through light exit aperture 32.

This makes it possible to even further inhibit stray light that has passed through through-hole 61 from leaking back out through through-hole 61 since the aperture area of through-hole 61 can be made smaller. This makes it possible to reduce noise generated by stray light even further.

Moreover, with particle sensor 1 according to this embodiment, first reflector 30 and second reflector 70 are distanced from each other.

This makes it possible to inhibit a reduction in reflection efficiency due to second reflector 70 becoming dirty due to particles collecting thereon since it is possible to inhibit particles in first reflector 30 from traveling to second reflector 70 by sufficiently distancing first reflector 30 and second reflector 70 from each other. As a result, detection accuracy remains stable over a long period of time, making it possible to achieve a particle sensor that has long-term reliability.

Moreover, with particle sensor 1 according to this embodiment, light attenuator 60 has first space 60a into which the light that has exited first reflector 30 enters and second space 60b into which light from first space 60a enters through through-hole 61, and second space 60b is a closed space.

This makes it possible to further effectively attenuate stray light that has entered second space 60b through through-hole 61. This makes it possible to reduce noise generated by stray light even further.

Moreover, with particle sensor 1 according to this embodiment, protrusion 62 is disposed at an edge of through-hole 61, on the second space 60b side of through-hole 61.

This makes it possible to inhibit light that has entered second space 60b from leaking from second space 60b through through-hole 61. This makes it possible to reduce noise generated by stray light even further.

Moreover, with particle sensor 1 according to this embodiment, light entrance aperture 31 and light exit aperture 32 are provided on the optical axis of light projector 10.

Light from light projector 10 that has entered first reflector 30 through light entrance aperture 31 and passed through detection area DA without striking particles in detection area DA becomes stray light and exits first reflector 30 through light exit aperture 32. With particle sensor 1 according to this embodiment, noise generated by such stray light can be significantly reduced.

Variation

Hereinbefore the particle sensor according to the present disclosure has been described based on an embodiment, but the present disclosure is not limited to the above embodiment.

For example, the particle sensor according to the above embodiment includes heater 40 and projection lens 50, but heater 40 and projection lens 50 may be omitted from the particle sensor.

Moreover, the particle sensor according to the above embodiment can be installed in a dust sensor. For example, when the dust sensor detects dust particles via the internal particle sensor, the detection of dust is notified via sound or light or displayed on a display.

Moreover, the particle sensor according to the above embodiment can be installed in a smoke detector. For example, when the smoke detector detects smoke particles via the internal particle sensor, the detection of smoke is notified via sound or light or displayed on a display.

Moreover, the particle sensor according to the above embodiment of the above dust sensor can be installed in an air purifier, ventilation fan, or air conditioner, for example. In such a case, when the air purifier, ventilation fan, or air conditioner detects dust via the internal particle sensor, simply the fact that dust has been detected may be displayed on the display, and the fan may be controlled, such as turning on a fan or changing the rotational speed of the fan.

While the foregoing has described one or more embodiments and/or other examples, it is understood that various modifications may be made therein and that the subject matter disclosed herein may be implemented in various forms and examples, and that they may be applied in numerous applications, only some of which have been described herein. It is intended by the following claims to claim any and all modifications and variations that fall within the true scope of the present teachings.

What is claimed is:

1. A particle sensor, comprising:
   a light projector that projects light to a detection area;
   a light receiver that receives scattered light, the scattered light being light from the light projector that has been scattered by particles in the detection area;
   a first reflector that reflects the scattered light to the light receiver;
   a light attenuator that attenuates stray light that exits the first reflector,
   wherein the first reflector includes a first aperture that introduces the light from the light projector into an interior of the first reflector and a second aperture that exits the stray light from the first reflector,
   the light attenuator includes a third aperture through which the stray light that exits the first reflector passes, and
   an aperture area of the third aperture is smaller than an aperture area of the second aperture; and
   a second reflector that reflects, to the third aperture, the stray light that exits the first reflector.

2. The particle sensor according to claim 1, wherein a barrier is disposed on a line connecting the second aperture and the third aperture.

3. The particle sensor according to claim 1, wherein the first reflector is spaced from the second reflector.

4. The particle sensor according to claim 1, wherein the light attenuator includes a first space and a second space which receive the stray light in order, and the second space is a closed space.

5. The particle sensor according to claim 4, wherein a protrusion is disposed at an edge of the third aperture, on a second space side of the third aperture.

6. The particle sensor according to claim 1, wherein the first aperture and the second aperture are aligned with an optical axis of the light projector.

7. The particle sensor according to claim 1, wherein the light attenuator includes a first space and a second space which receive the stray light in order, and the third aperture interconnects the first space and the second space.

8. The particle sensor according to claim 7, wherein the second reflector is disposed in the first space.

9. The particle sensor according to claim 8, wherein the first aperture, the second aperture, and the second reflector are aligned with an optical axis of the light projector.

10. The particle sensor according to claim 8, wherein the light attenuator further includes a protrusion in the second space, the protrusion being disposed on an edge of the third aperture.

11. The particle sensor according to claim 10, wherein the protrusion extends into the second space of the light attenuator parallel to an axis of the third aperture.

12. The particle sensor according to claim 10, wherein the second space of the third aperture is defined by three wall surfaces,
the third aperture extends through one of the three wall surfaces,
the protrusion is disposed on the one of the three wall surfaces on the edge of the protrusion, and
the three wall surfaces form a right triangle.

13. The particle sensor according to claim 12, wherein the right triangle formed by the three wall surfaces includes angles of thirty degrees, sixty degrees, and ninety degrees.

14. The particle sensor according to claim 12, wherein the one of the three wall surfaces that includes the third aperture and the protrusion is a leg of the right triangle.

15. The particle sensor according to claim 1, wherein the first reflector includes an elliptical mirror, the elliptical mirror including an inner surface that forms a segment of a spheroid.

16. A particle sensor, comprising:
a light projector that projects light to a detection area;
a light receiver that receives scattered light, the scattered light being light from the light projector that has been scattered by particles in the detection area;
a first reflector that reflects the scattered light to the light receiver; and
a light attenuator that attenuates stray light that exits the first reflector,
wherein the first reflector includes a first aperture that introduces the light from the light projector into an interior of the first reflector and a second aperture that exits the stray light from the first reflector,
the light attenuator includes a third aperture through which the stray light that exits the first reflector passes,
an aperture area of the third aperture is smaller than an aperture area of the second aperture, wherein the first reflector includes an elliptical mirror, the elliptical mirror including an inner surface that forms a segment of a spheroid, and
wherein the inner surface of the elliptical mirror includes a cross-sectional shape of a segment of an ellipse, and
among two focal points that define the ellipse, a first focal point is located in the detection area and a second focal point is located in a center of the light receiver.

17. The particle sensor according to claim 16, wherein the ellipse includes a major axis of 20 millimeters to 100 millimeters and a minor axis of 10 millimeters to 50 millimeters.

18. The particle sensor according to claim 1, wherein the light projector includes a light emitting diode or a laser diode, and
the light receiver includes a photodetector.

19. A particle sensor, comprising:
a light receiver configured to receive scattered light, the scattered light being light from a light projector that has been scattered by particles in a detection area;
a first reflector configured to reflect the scattered light to the light receiver;
a light attenuator configured to attenuate stray light that exits the first reflector,
wherein the first reflector includes a first aperture configured to introduce the light from the light projector into an interior of the first reflector and a second aperture configured to exit the stray light from the first reflector,
the light attenuator includes a third aperture configured to receive the stray light that exits the first reflector, and
a cross-sectional area of the third aperture is smaller than a cross-sectional area of the second aperture; and
a second reflector that reflects, to the third aperture, the stray light that exits the first reflector.

20. The particle sensor according to claim 1, wherein the stray light that enters the light attenuator is unwanted light.

21. The particle sensor according to claim 19, wherein the stray light that enters the light attenuator is unwanted light.

* * * * *